United States Patent [19]
Hardin et al.

[11] Patent Number: 6,001,657
[45] Date of Patent: Dec. 14, 1999

[54] ANTIBODIES THAT SELECTIVELY BIND QUADRUPLEX NUCLEIC ACIDS

[75] Inventors: Charles C. Hardin, Cary; Bernard A. Brown, II; John F. Roberts, both of Raleigh, all of N.C.; Stephen C. Pelsue, Portland, Me.

[73] Assignees: North Carolina State University, Raleigh, N.C.; Jackson Laboratories, Bar Harbor, Me.

[21] Appl. No.: 08/729,598

[22] Filed: Oct. 11, 1996

Related U.S. Application Data

[60] Provisional application No. 60/005,242, Oct. 12, 1995.

[51] Int. Cl.$^6$ ............... G01N 33/566; G01N 33/551; G01N 33/552; G01N 33/536
[52] U.S. Cl. ............... 436/501; 436/508; 436/518; 436/527; 436/524; 436/529; 436/532; 436/533; 436/536; 436/538; 436/548; 530/388.21
[58] Field of Search ............... 530/388.21; 436/508, 436/518, 524, 527, 529, 532, 533, 536, 538, 548, 501

[56] References Cited

U.S. PATENT DOCUMENTS 4,732,847  3/1988  Stuart et al. .

OTHER PUBLICATIONS

Andrzejewski, et al. "Hybridoma Autoantibodies to DNA", *The Journal of Immunology*, vol. 24, No. 3 (Mar. 1980), pp. 1499–1502.
Lafer, et al., "Antibodies specific for left–handed Z–DNA", *Proc. Natl. Acad. Sci., USA*, vol. 78, No. 6 (Jun. 1981), pp. 3546–3550.
Hardin, et al., "Stabilization of Z–RNA by Chemical Bromination and Its Recognition by Anti–Z–DNA Antibodies", *Biochemistry*, vol. 26, No. 16 (1987), pp. 5191–5199.
Hardin, et al., "Characterization of Anti–Z–RNA Polyclonal Antibodies: Epitope Properties and Recognition of Z–DNA", *Biochemistry*, vol. 27, No. 11 (1988), pp. 4169–4177.

Huse, et al., "Generation of a Large Combinatorial Library of the Immunoglobulin Repertoire in Phage Lambda", *Science*, vol. 246 (Dec. 1989), pp. 1275–1281 and 1250–1251.
Hardin, et al., "Monovalent Cation Induced Structural Transitions in Telomeric DNAs: G–DNA Folding Intermediates", *Biochemistry*, vol. 30, No. 18 (1991), pp. 4460–4472.
Hardin, et al., "Cation–Dependent Transition between the Quadruplex and Watson–Crick Hairpin Forms of d(CGCG$_3$GcG)", *Biochemistry*, vol. 31, No. 3 (1992), pp. 833–841.
Weisman–Shomer, et al., "QUAD, a Protein from Hepatocyte Chromatin That Binds Selectively to Guanine–rich Quadruplex DNA", *The Journal of Biological Chemistry*, vol. 268, No. 5 (Feb. 1993), pp. 3306–3312.
Hardin, et al., "Cytosine–Cytosine$^+$ Base Pairing Stabilizes DNA Quadruplexes and Cytosine Methylation Greatly Enhances the Effect", *Biochemistry*, vol. 32, No. 22 (1993), pp. 5870–5880.
Macaya, et al., "Thrombin–binding DNA aptamer forms a unimolecular quadruplex structure in solution", *Proc. Natl. Acad. Sci. USA*, vol. 90 (Apr. 1993), pp. 3745–3749.
Schierer et al., "A Protein from *Tetrahymena thermophila* That Specifically Binds Parallel–Stranded G4–DNA", *Biochemistry*, vol. 33, No. 8 (1994), pp. 2240–2246.
Ross et al., "Ion–Induced Stabilization of the G–DNA Quadruplex: Free Energy Perturbation Studies", *J. Am. Chem. Soc.*, vol. 116, No. 14 (1994), pp. 6070–6080.
Weisman–Shomer, et al., "Stabilization Of Tetrahelical DNA By The Quadruplex DNA Binding Protein QUAD", *Biochemical and Biophysical Research Communications*, vol. 205, No. 1 (Nov. 1994), pp. 305–311.
Huizenga, et al. "A DNA Aptamer That Binds Adenosine and ATP", *Biochemistry*, vol. 34, No. 2 (1995), pp. 656–665.
Hermann, et al., "Preferential recognition of specific DNA motifs by anti–double–stranded DNA autoantibodies", *Eur. J. Immunol.*, vol. 25 (1995), pp. 1897–1904.

*Primary Examiner*—Sheela Huff
*Assistant Examiner*—Geetha P. Bansal
*Attorney, Agent, or Firm*—Myers Bigel Sibley & Sajovec

[57] ABSTRACT

Antibodies that selectively bind to quadruplex nucleic acids are described. Isolated cells that produce such antibodies, and methods utilizing these antibodies, are also described.

9 Claims, 1 Drawing Sheet

FIG. 1

ANTIBODIES THAT SELECTIVELY BIND QUADRUPLEX NUCLEIC ACIDS

This application claims the benefit of U.S. Provisional Application No. 60/005,242, filed on Oct. 12, 1995.

This invention was made with Government support under grant number GM47431 from the National Institutes of Health. The Government has certain rights to this invention.

FIELD OF THE INVENTION

This invention relates to antibodies that bind selectively and preferentially to quadruplex nucleic acids. Immunoassays and other methods utilizing the quadruplex nucleic acid-binding antibodies are also disclosed.

BACKGROUND OF THE INVENTION

Telomeric and other guanine-rich DNAs can form a variety of novel four-stranded structures containing G—G base pairs that are stabilized by physiologically important cations such as $Na^+$ and $K^+$. See, e.g., E. Henderson, et al., *Cell* 51, 899–908 (1987); Y. Oka and C. A. Thomas, *Nucleic Acids Res.* 15, 8877–8898 (1987); D. Sen and W. Gilbert, *Nature* 334, 364–366 (1988). A number of quadruplex conformational variants have been described and several biological and biotechnological roles have been suggested, including telomere-telomere interactions, telomerase inhibition, chromatin condensation, aptamer structure, mitotic and meiotic chromosomal pairing, promotion of recombination, eukaryotic intron RNA recognition, and repression of eukaryotic transcription and viral replication. See. e.g., E. Henderson et al., supra; M. K. Raghuraman and T. R. Cech, *Nucleic Acids Res.* 18, 4543–4552 (1990); E. H. Blackburn, *J. Biol. Chem.* 265, 5919–5921 (1990); D. E. Huizenga and J. W. Szostak, *Biochemistry* 34, 656–665 (1995); R. F. Macaya et al., *Proc. Natl. Acad. Sci. USA* 90, 3745–3749 (1993); A. T. Pluta and V. A. Zakian, *Nature* 337, 429–33 (1989); N. Abdul-Manan, et al., *Biochemistry* 35, 3545–3554 (1996).

In vitro studies of a consensus SP1 transcription factor binding sequence motif oligonucleotide, d(CGC $G_4$ GCG) (abbreviated $G_4$-DNA, SEQ ID NO:1), have shown that four of these oligonucleotides form a parallel intramolecular quadruplex at moderate ionic strengths. See, C. C. Hardin et al., *Biochemistry* 32, 5870–5880 (1993); D. R. Goodlet et al., *Biol. Mass. Spec.* 22, 181–183 (1993). Circular dichroism and NMR studies have shown that this quadruplex is inherently stable ($T_m$ of ca. 90° C.) when formed in 20 mM $K^+$. The biological roles of such a stable complex are clearly worthy of probing, yet definitive detection of these structures in vivo has heretofore not been accomplished.

Several studies have demonstrated the utility of antibodies in elucidating structural features of native and modified nucleic acids. See C. C. Hardin et al., *Biochemistry* 27, 4169–4177 (1988). Right- and left-handed RNAs and DNAs and triplex DNAs have been studied in vitro and in vivo using polyclonal and monoclonal antibodies. Id.; see also E. M. Lafer et al., *Proc. Natl. Acad. Sci. USA* 78, 3546–3550 (1981); C. C. Hardin et al., *Biochemistry* 26, 5191–5199 (1987). Anti-DNA antibodies have been obtained from murine models of systemic lupus erythematosus (SLE). Specifically, $(NZB/NZW)F_1$ and MRL/Mp-lpr/lpr mice have been shown to produce antibodies that are specific for single- and double-stranded DNA, Z-DNA, RNA and rRNA. See, e.g., C. Andrzejewski et al., *J. Immunol.* 124, 1499–1502 (1980); M. Herrmann et al., *Eur. J. Immunol.* 25, 1897–1904 (1995). However, the production of antibodies useful in detecting and characterizing quadruplex nucleic acids has heretofore proved elusive. Accordingly, there exists a need for means and methods to easily detect and study quadruplex nucleic acids, in order to further elucidate the biological functions related thereto.

SUMMARY OF THE INVENTION

The present invention is based on the discovery of antibodies that selectively bind to quadruplex nucleic acids. Accordingly, a first aspect of the invention is an isolated antibody that selectively binds to quadruplex nucleic acid.

A second aspect of the present invention is an isolated cell that produces an antibody that selectively binds to quadruplex nucleic acid.

A third aspect of the present invention is a method of binding quadruplex nucleic acid, comprising providing an antibody that selectively binds to quadruplex nucleic acid, and then contacting the quadruplex nucleic acid to the antibody to form an antibody-quadruplex nucleic acid complex. The method is useful both in detecting antibodies that bind to quadruplex nucleic acids, and in collecting antibodies that bind to quadruplex nucleic acids.

BRIEF DESCRIPTION OF THE DRAWINGS

In FIG. 1, the substrate-antibody binding parameters of functional equilibrium constant (Ka), a measure of binding affinity, is plotted as a function of the substrate structure. In this figure, the symbol (■) refers to the quadruplex $[(TET4)_4]$ (SEQ ID NO:3)$_4$; the symbol (♦) refers to the quadruplex $[d(TG_4)_4]$ (SEQ ID NO:2)$_4$; the symbol (●) refers to the quadruplex $[(d(CGC\ G_4\ GCG)_4])$ (SEQ ID NO:1)$_4$; the symbol (□) refers to the triplex $d(G_4T_3G_4T_3C_4)$ (SEQ ID NO:11); the symbol (O) refers to the triplex $d(C_4T_3G_4T_3G_4)$ (SEQ ID NO:12); the symbol ((▷)) refers to the duplex $[d(CG5)_2]$ (SEQ ID NO:13)$_2$; the symbol (Δ) refers to the single strand poly $[r(G)]$; and the symbol (▽) refers to the single strand poly $[r(C)]$.

DETAILED DESCRIPTION OF THE INVENTION

The term "antibodies," as used herein, refers to all types of immunoglobulins, including IgG, IgM, IgA, IgD, and IgE, and includes antibody fragments such as, e.g., Fab, F(ab')$_2$, and Fc fragments, and the corresponding fragments obtained from antibodies other than IgG. The antibodies of the present invention may be monoclonal or polyclonal, and may be of any species of origin, including (for example) mouse, rat, rabbit, horse, or human. Antibodies according to the present invention may also be chimeric antibodies, e.g., recombinant antibodies wherein the binding regions of an antibody are fused to another protein. See, e.g., M. Clark, PCT Application No. WO 92/16562; H. Waldman, PCT Application No. WO 93/01289; and M. Walker et al., *Molecular Immunology* 26, 403–41 (1989).

As used herein, the term "nucleic acids" refers to RNAs and DNAs, and includes both natural and modified RNAs and DNAs.

This invention relates to antibodies that selectively bind to quadruplex nucleic acids (sometimes also called tetraplex nucleic acids). Such antibodies, as defined herein, are antibodies that bind preferentially and specifically to quadruplex nucleic acids, but exhibit significantly lower affinity for, and preferably, essentially no binding to triplex, duplex and single-stranded nucleic acids of the same primary sequence or base composition under essentially the same binding conditions. Thus, an antibody that selectively binds quadruplex nucleic acids or quadruplex nucleic acid isoforms (i.e., the ligand) generally refers to a molecule capable of reacting with or otherwise recognizing or binding such a ligand. An antibody selectively binds a ligand, has binding affinity for a ligand, or is specific for a ligand if the antibody binds or is capable of binding the ligand as measured or determined by standard antibody-antigen or ligand-receptor assays, e.g., competitive assays, saturation assays, or standard immunoassays such as ELISA, RIA, or radio-immuno-filter binding (RIFB) assays. Purified antibodies of the present invention that selectively bind quadruplex nucleic acids will have at least a two-fold higher affinity for quadruplex nucleic acid than for single-stranded, duplex and triplex nucleic acid structures of similar base composition and length, will more preferably have at least a ten-fold higher affinity for quadruplex nucleic acids than for the other structures, and will most preferably have at least a twenty-fold higher affinity for quadruplex nucleic acids than for the other structures.

Quadruplex nucleic acids that are bound by antibodies of the present invention may comprise four separate nucleic acid strands that are joined together in a quadruplex structure known to those skilled in the art. Such quadruplex structures include, but are not limited to, single-stranded antiparallel intramolecular quadruplexes (e.g., $[d(T_2G_4T_2G_4T_2G_4T_2G_4)_4]$, or $(TET4)_4$ (SEQ ID NO:3)$_4$ and parallel-stranded intramolecular quadruplexes (e.g., $[d(CGC\ G_4\ GCG)_4]$) (SEQ ID NO:1)$_4$.

As used herein, one strand of quadruplex nucleic acid may contain a minimum of one nucleotide or nucleoside per strand, but more preferably contains at least three (3) nucleotides or nucleosides per strand, and most preferably contains at least six (6) nucleotides or nucleosides per strand. As used herein, one strand of quadruplex nucleic acid may contain up to fifty (50) nucleotides or nucleosides per strand, but more preferably contains at most thirty-two (32) nucleotides or nucleosides per strand, and most preferably contains at most twenty-four (24) nucleotides or nucleosides per strand. Quadruplex nucleic acids bound by antibodies of the present invention may be contained within a larger nucleic acid segment, which may be, in the case of DNA, as large as a complete chromosome. Exemplary quadruplex nucleic acids of the present invention include, but are not limited to, the following:

(1) $[d(CGCGGGGCG)_4]$, or $[d(CGC\ G_4\ GCG)_4]$ (SEQ ID NO:1)$_4$;
(2) $[d(TGGGG)_4]$, or $[d(TG_4)_4]$ (SEQ ID NO:2)$_4$;
(3) $[d(TTGGGGTTGGGGTTGGGGTTGGGG)_4]$, or $[d(T_2G_4T_2G_4T_2G_4T_2G_4)_4]$, or $(TET4)_4$ (SEQ ID NO:3)$_4$;
(4) $[d(TTAGGG)_4]$, or $[d(T_2\ AG_4)_4]$ (SEQ ID NO:4)$_4$;
(5) $[d(CGCGGGGCG)_4]$, or $[d(CGC\ G_3\ GCG)_4]$ (SEQ ID NO:5)$_4$;
(6) $[d(TATGGGGATA)_4]$, or $[d(TAT\ G_4\ ATA)_4]$ (SEQ ID NO:6)$_4$;
(7) $[d(AGGGGGGGAGAGGGGGGAGGGGGG)_4]$, or $[d(AG_6\ GAG\ AG_6\ AG_6)_4]$ (SEQ ID NO:7)$_4$;
(8) $[d(TTTAGGG)_4]$, or $[d(T_3\ A\ G_3)_4]$ (SEQ ID NO:8)$_4$,
(9) $[d(TTTTGGGG)_4]$, or $[d(T_4G_4)_4]$ (SEQ ID NO:9)$_4$;
(10) $[r(UGGGG)_4]$, or $[r(UG_4)_4]$ (SEQ ID NO:10)$_4$;
(11) $[GMP_4]$, or $[(guanine\ monophosphate)_4]$ In the foregoing, each sequence contained within the parentheses refers to the sequence of a separate strand of nucleic acid, but may alternatively refer to one unit of a repeating unit contained within one strand of nucleic acid.

Monoclonal antibodies used to carry out the present invention may be produced in a hybridoma cell line according to the techniques of Kohler and Milstein (*Nature* 265, 495–97 (1975); *Eur. J. Immunol.* 137, 216–222 (1976)), with a lymphocyte from an appropriate donor animal. In a preferred embodiment, lymphocytes are taken from the lymph nodes of an immunodeficient, autoimmune animal such as "motheaten" mouse or the "viable motheaten" mouse, and the lymphocytes then immortalized by fusing them with an immortal cell (e.g., myeloma cell or lymphoma cell), typically in the presence of polyethylene glycol, to produce hybridoma cells. The hybridoma cells are then grown in a suitable media and the supernatant screened for monoclonal antibodies having the desired specificity.

Monoclonal Fab fragments may be produced in a host cell such as *Escherichia coli* or yeast (e.g., *Saccharomyces cerevisiae, S. pombe*, etc.) from the known sequences of monoclonal antibodies by recombinant techniques known to those skilled in the art. See, e.g., W. Huse, *Science* 246, 1275–81 (1989). The DNA encoding one antibody can be obtained and converted to another antibody by site-directed mutagenesis. See, e.g., T. Kunkel et al., *Methods in Enzymol.* 154, 367–382 (1987); T. Kunkel, U.S. Pat. No. 4,873,192 (applicant specifically intends the disclosure of this and all other patents cited herein be incorporated herein, in its entirety, by reference).

The present invention may further comprise a method of binding an antibody as described herein with quadruplex nucleic acids. In general, the method of binding quadruplex nucleic acids comprises providing an antibody that selectively binds to quadruplex nucleic acid, and then contacting the quadruplex nucleic acid to the antibody to form an antibody-quadruplex nucleic acid complex. This binding step may be carried out for a number of purposes, including the detection of quadruplex nucleic acids or the purification of quadruplex nucleic acids.

In a preferred embodiment of the invention, the detection of quadruplex nucleic acids may be carried out by immunoassay. Generally, in the case of an immunoassay, the binding step is followed by the step of detecting said antibody-quadruplex nucleic acid complex with, for example, an enzyme-linked immunosorbent assay. In another preferred embodiment of the invention, the purification of quadruplex nucleic acids may be carried out by affinity purification. Generally, in the case of affinity purification, the binding step as described above is followed by collecting said quadruplex nucleic acids from said antibody-quadruplex nucleic acid complex. As an example, the antibody is immobilized on a solid support, and the collecting step is carried out by eluting said quadruplex nucleic acids from the solid support.

The detection of the presence or absence of quadruplex nucleic acids may be carried out either directly or indirectly by any suitable means. A variety of techniques are known to those skilled in the art. All generally involve the step of collecting a sample of biological material suspected of containing quadruplex nucleic acids, and then detecting whether or not the subject possesses quadruplex nucleic acids in that sample. For example, the detecting step may be carried out by collecting a biological sample from a subject (for example, from cerebrospinal fluid, or any other fluid or tissue containing suspected of containing quadruplex nucleic acid), and then determining the presence or absence of quadruplex nucleic acids in the sample (e.g., by immunoassay).

Any biological sample which may contain quadruplex nucleic acids may be employed, including tissue samples and blood samples, with blood cells and sera being particularly convenient sources.

The step of determining the presence or absence of quadruplex nucleic acids in a sample may be carried out by an antibody assay with an antibody that selectively binds to quadruplex nucleic acids (i.e., an antibody which binds preferentially and specifically to quadruplex nucleic acids but exhibits essentially no binding to triplex, duplex and single-stranded nucleic acids with similar sequences and base composition under the same binding conditions).

Antibody assays (immunoassays) may, in general, be homogeneous assays or heterogeneous assays. In a homogeneous assay the immunological reaction usually involves the specific antibody, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels which may be employed include free radicals, radioisotopes, fluorescent dyes, enzymes, bacteriophages, coenzymes, and so forth.

In a heterogeneous assay approach, the reagents are usually the specimen, the antibody of the invention and a system or means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the specimen. Means for producing a detectable signal include the use of radioactive labels, fluorescent labels, enzyme labels, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Those skilled in the art will be familiar with numerous specific immunoassay formats and variations thereof which may be useful for carrying out the method disclosed herein. See generally, E. Maggio, *Enzyme-Immunoassay,* (1980) (CRC Press, Inc., Boca Raton, Fla.); see also U.S. Pat. No. 4,727,022 to Skold et al.; U.S. Pat. No. 4,659,678 to Forrest et al., U.S. Pat. No. 4,376,110 to David et al., U.S. Pat. No. 4,275,149 to Litman et al., U.S. Pat. No. 4,233,402 to Maggio et al., and U.S. Pat. No. 4,230,767 to Boguslaski et al.

Antibodies that selectively bind quadruplex nucleic acids (i.e., an antibodies that bind preferentially and specifically to quadruplex nucleic acids but exhibit essentially no binding to triplex, duplex and single-stranded nucleic acids with similar sequences and base composition under the same binding conditions) may be conjugated to a solid support suitable for a diagnostic assay (e.g., beads, plates, slides or wells formed from materials such as latex or polystyrene) in accordance with known techniques, such as precipitation. Antibodies which bind quadruplex nucleic acids may likewise be conjugated to detectable groups such as radiolabels (e.g., $^{35}S$, $^{125}I$, $^{131}I$), nucleic acids, enzyme labels (e.g., horseradish peroxidase, alkaline phosphatase), and fluorescent labels (e.g., fluorescein) in accordance with known techniques.

Kits for determining if a sample contains quadruplex nucleic acids will include at least one reagent specific for detecting for the presence or absence of quadruplex nucleic acids and instructions for observing that the sample does or does not contain quadruplex nucleic acids.

Diagnostic kits for carrying out antibody assays may be produced in a number of ways. In one embodiment, the diagnostic kit comprises (a) an antibody which binds quadruplex nucleic acids conjugated to a solid support and (b) a second antibody which binds quadruplex nucleic acids conjugated to a detectable group. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. A second embodiment of a test kit comprises (a) an antibody as above, and (b) a specific binding partner for the antibody conjugated to a detectable group. Ancillary agents as described above may likewise be included. The test kit may be packaged in any suitable manner, typically with all elements in a single container along with a sheet of printed instructions for carrying out the test.

The immunochemical assay comprises optionally (but preferably) combining a sample that contains antibody selectively bound to quadruplex nucleic acids (such as a blood sample) with a reducing agent, then contacting the sample to a solid support which specifically binds reactive sulfhydryl groups, then separating the sample from the solid support; and then detecting by immunoassay either (i) the presence or absence of antibody that selectively binds quadruplex nucleic acids in said sample, or (ii) the presence or absence of antibody that selectively binds quadruplex nucleic acids immobilized on the solid support.

The immunoassay step is carried out by binding a detecting antibody with an antibody that specifically binds to quadruplex nucleic acids. The detecting antibodies include all types of immunoglobulins, including IgG, IgM, IgA, IgD, and IgE produced by any known suitable method as described above.

Immunoassays may, in general, be homogeneous assays or heterogeneous assays, as described above. As also described above, antibodies which specifically bind quadruplex nucleic acids may be conjugated to a solid support suitable for a diagnostic assay (e.g., beads, plates, slides or wells formed from materials such as latex or polystyrene) in accordance with known techniques, and they may likewise be conjugated to detectable groups.

Diagnostic kits for carrying out the immunochemical assay may be produced in a number of ways. In one embodiment, the kit comprises (a) a solid support that specifically binds reactive sulfhydryl groups, (b) an detecting antibody that binds to an antibody that selectively binds quadruplex nucleic acids and (c), optionally, a reducing agent. In another embodiment, the diagnostic kit comprises (a) a detecting antibody that binds to antibody that selectively binds quadruplex nucleic acids conjugated to a solid support and (b) a second antibody which selectively binds quadruplex nucleic acids, conjugated to a detectable group. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. A third embodiment of a test kit comprises (a) a detecting antibody as above, and (b) a specific binding partner for the antibody conjugated to a detectable group. Ancillary agents as described above may likewise be included. The test kit may be packaged in any suitable manner, typically with all elements in a single container along with a sheet of printed instructions for carrying out the test.

Isolated DNA encoding an antibody that selectively binds quadruplex nucleic acids is defined as DNA selected from the group consisting of: (a) isolated DNA that encodes an antibody that selectively binds quadruplex nucleic acids, (e.g., an antibody that binds to [d(CGCGGGGGCG)$_4$] (SEQ ID NO:1)$_4$ (b) isolated genomic DNA which hybridizes to isolated DNA of (a) above under conditions represented by a wash stringency of 0.3M NaCl, 0.03M sodium citrate, and 0.1% SDS at 60° C., which is at least 65% homologous to the isolated DNA of (a) above (i.e., 65% homologous or more with respect to total DNA sequence; homology with respect to exon sequence alone is about 93% or more), and which encodes an antibody that selectively binds to quadruplex nucleic acids and (c) isolated DNA differing from the isolated DNAs of (a) and (b) above in nucleotide sequence due to the degeneracy of the genetic code, and which encodes an antibody that binds selectively to quadruplex nucleic acids.

DNAs which encode antibodies that selectively bind quadruplex nucleic acids, whether they are cDNAs or intron-containing genomic DNAs, encode an antibody that, on expression in a suitable host cell, selectively and stereospecifically binds quadruplex nucleic acids. This definition is intended to encompass natural allelic variations in the DNAs. Genomic DNAs of the present invention may code for an antibody that selectively binds quadruplex nucleic acids of any species of origin, including mouse, rat, rabbit, cat, porcine, and human, but preferably code for an antibody that selectively binds quadruplex nucleic acids of mammalian origin, and most preferably code for a human antibody that selectively binds quadruplex nucleic acids. Complementary DNAs of the present invention encode antibodies that selectively bind quadruplex nucleic acids. Hybridization conditions which will permit other DNA sequences which code for expression of an antibody that selectively binds quadruplex nucleic acids to hybridize to a DNA sequence as given herein are, in general, high stringency conditions. For example, hybridization of such sequences may be carried out under conditions represented by a wash stringency of 0.3 M NaCl, 0.03 M sodium citrate, 0.1% SDS at 60° C. or even 70° C. to DNA disclosed herein in a standard in situ hybridization assay. See J. Sambrook et al., *Molecular Cloning, A Laboratory Manual* (2d Ed. 1989) (Cold Spring Harbor Laboratory)). The same hybridization conditions are used to determine hybridization of oligonucleotides.

In general, genomic DNA sequences which code for antibody that selectively binds quadruplex nucleic acids and hybridize to the genomic DNA sequence encoding antibody that selectively binds quadruplex nucleic acids disclosed herein will be at least 65%, 70%, 75%, 80%, 85%, 90%, or even 95% homologous or more with the sequence of the genomic DNA encoding the antibody that selectively binds quadruplex nucleic acids disclosed herein (with respect to the total genomic DNA). These same levels of homology apply to oligonucleotide probes which hybridize to the introns of the genomic DNA sequences disclosed herein. Homology among the exons alone between various human genomic DNA sequences encoding the antibody that selectively binds quadruplex nucleic acids are contemplated to be of the same order as given below with respect to cDNA sequences.

Further, DNA sequences (or oligonucleotides) that code for the same antibody that selectively binds quadruplex nucleic acids (or fragment thereof) as coded for by the foregoing sequences, but which differ in codon sequence from these due to the degeneracy of the genetic code, are also an aspect of this invention. The degeneracy of the genetic code, which allows different nucleic acid sequences to code for the same protein or peptide, is well known in the literature. See e.g., U.S. Pat. No. 4,757,006 to Toole et al. at Col. 2, Table 1.

This invention provides antibodies that are useful in many practical applications. For example, antibodies of the present invention may be used in the affinity purification of quadruplex nucleic acids from solutions. As aptamers (DNA or RNA nucleotides that have been screened from a randomly generated population of sequences for their ability to bind a desired molecular target) are known to contain quadruplex nucleic acid structures, the antibodies of the present invention may also be used to purify aptamers from combinatorial libraries or heterogenous solutions, or may be further used to detect the presence or absence of aptamers in said solutions or libraries. In a related use, the antibodies of the present invention may be used to purify or detect DNA aptamers that specifically bind the thrombin molecule, which is critical in the thrombin-catalyzed, fibrin-clot formation cascade of blood platelets (see R. F. Macaya et al., *Proc. Natl. Acad. Sci. USA* 90, 3745–3749 (1993)). This particular example is indicative of the general use of the antibodies of the present invention to detect levels of known therapeutic aptamer in a patient, and thus monitor clearance and dosage levels of the quadruplex-nucleic acid-containing aptamer in a treatment protocol involving the aptamer.

The present invention is explained in greater detail in the following non-limiting Examples. As used below, EDTA means ethylenediaminetetraacetic acid, FBS means fetal bovine serum, NMR means nuclear magnetic resonance, PBS means phosphate-buffered saline, TBS means tris-buffered saline, TSP means sodium 3-(trimethylsilyl)-1-propanesulfonic acid, mM means millimolar, ° C. means degrees Celsius, UV means ultraviolet, ELISA means enzyme-linked immunosorbent assay, nm means nanometers, mL means milliliters, $\mu$L means microliters, $\mu$g means micrograms, $cm^2$ means centimeters-squared, m means minutes and h means hours.

EXAMPLE 1

Oligonucleotide Preparation and Analyses

Oligonucleotides were synthesized in the North Carolina State University (Raleigh, N.C.) Molecular Genetics Facility using standard cyanoethyl phosphoramidite methods. The reaction products were suspended in concentrated ammonium hydroxide, then lyophilized to dryness and dialyzed against 200 mM KCl to stabilize quadruplex formation or 200 mM NaCl to prepare the other complexes (e.g., triplexes). Samples were redried, then dialyzed extensively against 0.1 mM $K_2$EDTA (pH 7) or 0.1 mM $Na_2$EDTA (pH 7). Purified stocks were stored for use at 4° C. Concentrations were determined by UV absorbance, assuming that an absorbance of one at 260 nm is equal to 34.8 $\mu$g DNA, as calculated using the program OLIGO 4.02 (National Biosciences, Inc.). Sample purity and integrity was verified by NMR, circular dichroism (CD), and gel electrophoretic analyses.

EXAMPLE 2

Preparation of Anti-DNA Quadruplex Hybridomas

"Viable motheaten" mice, C57BL/6J-me$^v$/me$^v$, were generously donated by Drs. Stephen Pelsue and Leonard Shultz (The Jackson Laboratory, Bar Harbor, Me.). Two three-month-old me$^v$ mice were caged in a sterile isolator cage and fed autoclaved food and water ad libitum. The mice were maintained about one week after arrival then used for hybridoma fusions. Mice were not immunized prior to lymph node isolation. Cells isolated from cervical and mesenteric lymph nodes were fused with non-secreting BALB/c plasmacytoma cells (P3-X63-Ag8.653) according to standard protocols (see G. Kohler and C. Milstein, *Nature* 256, 495–497 (1975); G. Kohler and C. Milstein, *Eur. J. Immunol.* 137, 216–222 (1976)). After fusion, cells were dispensed into 24-well microtiter plates and selected in HAT media (RPMI-1640 media (Mediatech) containing: 100 μM hypoxanthine, 40 μM aminopterin, 16 μM thymidine, 2 mM glutamine, 10% FBS) for 12 days, then switched to HT media (RPMI-1640 media containing: 100 μM hypoxanthine, 16 μM thymidine, 2 mM glutamine, 10% FBS) for 10 days. Surviving hybridomas were maintained in RPMI-1640 media supplemented with 2 mM glutamine and 5% FBS at 37° C. in a humidified incubator under air and 5% $CO_2$.

Antibody production was detected by removing 1 mL of media from each individual culture (usually prior to feeding) and assaying by radio-immuno-filter-binding (RIFB) assays. Cultures which exhibited anti-[d(CGC $G_4$ GCG)$_4$] (SEQ ID NO:1)$_4$ quadruplex binding reactivity were expanded in 25 and 75 cm$^2$ tissue culture flasks. Monoclonal anti-DNA quadruplex hybridomas were obtained by sequential limiting dilution cloning (see G. Galfre and C. Milstein, *Methods Enzymol.* 73, 3–46 (1981); F. M. Ausubel et al., *Short Protocols in Molecular Biology*, 2nd Ed., November28/November 29 (John Wiley and Sons, New York 1992). Frozen stocks of about 10$^6$ cells in 92% FBS, 8% DMSO were stored in liquid $N_2$.

EXAMPLE 3

Immunochemical Assays

ELISA and RIFB assays were performed on tissue culture supernatants to detect antibody titers by modifying procedures of C. C. Hardin et al., *Biochemistry* 27, 4169–4177 (1988), and A. Möller et al., *J. Biol. Chem.* 257, 12081–12085 (1982). Anti-DNA IgM (Boehringer-Mannheim; 50 μg/mL in PBS) was used as a positive control for double-stranded DNA binding. Sera specific for double- and single-stranded DNAs from autoimmune MLR/Mp-lpr/lpr mice were generously donated by Drs. Elizabeth Reap and Phil Cohen (Dept. of Rheumatology, University of North Carolina, Chapel Hill, N.C.), and were also used as controls.

ELISAs were performed at room temperature, using 150 μL volumes unless otherwise noted. Poly-L-lysine (100 μL; 50 μg/mL in deionized $H_2O$) was dispensed into sterile 96-well polystyrene microtiter plates and incubated for 30 m. Plates were then washed twice with TEP buffer (50 mM Tris-HCl (pH 7.4), 5 mM EDTA, 150 mM KCl) and allowed to dry briefly. Control DNAs (100 μl of 10 μg/mL in $H_2O$) were aliquotted into the wells and incubated for 2 h followed by two washes with TEP. Nonspecific adsorption was blocked by incubating the wells with 100 μL 50 μg/mL poly-L-glutamate in TEP for one hour, followed by a second blocking with 2% non-fat powdered milk in TEP for 30 m. Wells were washed once with TEPT (TEP containing 0.1% Tween-20), then twice with TEP between and after each blocking step. Antigen-coated wells were incubated for at least 90 m at 37° C. with 100 μL tissue culture media supernatants or purified antibodies. Wells were washed once with TEPT, followed by two washes with TEP. Goat anti-mouse polyvalent (IgM, IgG, and IgA)-alkaline phosphatase immunoconjugate (Sigma) was aliquotted (100 μL; 2000-fold diluted with TEP) into wells and incubated for 90 m at 37° C., followed by one wash with TEPT then two washes with TEP. Finally, 50 μL of p-nitrophenyl phosphate (1 mg/mL n 50 mM $NaHCO_3$ (pH 9.5) containing 2 mM $MgCl_2$) was added and samples were incubated for 1 h at 25° C. Reactions were stopped by adding 100 μL of 4 N NaOH. Absorbances at 405 nm were read directly in a Bio-TEK EL340 Microplate Reader interfaced to a 486 PC controlled by Kineti-Calc 2.14 software.

RIFB assays were performed in sterile, siliconized 0.5 mL microcentrifuge tubes. Tissue culture supernatants or purified antibodies (100 μL) were incubated for 1 hour at 37° C. with 10–5000 ng (approximately 0.5–80 nanomoles) of $^{32}P$ end-labeled competitive DNA substrate in TEP buffer. Following incubation, reactions were transferred to individual wells of Multiscreen®-HA (0.45 μm nitrocellulose) microtiter filtration plates (Millipore), which had been pre-soaked with TBS for 10 m. Reactions were incubated in the plate for 10 m at 25° C., then aspirated through the filters by vacuum. All filters were washed once with TBST, followed by four washes with TBS and then air-dried at room temperature for 30 m. Individual filters were punched out and counted by liquid scintillation in 1 mL of scintillation cocktail (Fisher).

EXAMPLE 4

Detection of Anti-DNA Quadruplex Antibodies

An autoantibody with specificity for DNA quadruplexes was isolated and cloned from a hybridoma fusion preparation of cervical and mesenteric lymph nodes from two, three-month-old viable motheaten mice. This antibody (me$^v$-$\alpha Q_1$) was detected by assaying tissue culture media directly from each sample well of Example 3 by ELISA and RIFB assay. Specifically, anti-quadruplex antibodies were detected by assaying culture supernatants obtained from each well of the tissue culture plate using radiolabeled [d(CGC $G_4$ GCG)$_4$] (SEQ ID NO:1)$_4$ in RIFE assays. The self-complementary intermolecular duplex, [d(CGCGCGCGCG)$_2$] (or, [d(CG5)$_2$] (SEQ ID NO:13)$_2$), was used as a negative control to select against anti-G-rich duplex antibodies. During the initial screening of the moth-eaten fusion library, four cultures displayed anti-[d(CGC $G_4$ GCG)$_4$] (SEQ ID NO:1)$_4$ binding activities above baseline levels. Three cultures had anti-DNA quadruplex activities and low anti-double-stranded activities. One culture had binding affinity for quadruplex DNA that was about 5-fold higher than the baseline level. This culture was expanded, rendered monoclonal by limited dilution culturing, and propagated for use.

In additional studies, the me$^v$-$\alpha Q_1$ antibody was found to bind preferentially and specifically to quadruplex DNA when compared to triplex, duplex and single-stranded DNAs with similar sequences and base composition, as detailed below in Example 5.

EXAMPLE 5

Specificity of Recognition of Quadruplex DNA by an Anti-Quadruplex Antibody

Binding specificities of the anti-quadruplex antibody me$^v$-$\alpha Q_1$ for quadruplex DNAs relative to triplex, duplex, and single-stranded DNAs were determined by RIFB competition assays (C-RIFB). These assays were performed essentially as described above with minor modifications. Ten ng/µL of $^{32}$P end-labeled quadruplex samples, [(TET4)$_4$] (SEQ ID NO:3)$_4$, [d(TG$_4$)$_4$] (SEQ ID NO:2)$_4$, or [d(CGC G4 GCG)$_4$] (SEQ ID NO:1)$_4$, in 50 µL of TEP buffer were incubated at 37° C. with 100 µL tissue culture supernatant samples or 100 µL purified antibody samples containing 1 mg/mL protein. Unlabeled competitor DNAs (0–5000 ng) were added and the reactions were incubated at 37° C. for 1 hr, then transferred to individual wells or pre-soaked MultiScreen® filtration plates and treated as described above. The results of the C-RIFB assays demonstrated that me$^v$-αQ$_1$ remains bound to each of the quadruplexes in the presence of 100-fold excess competitor DNA by weight. Moreover, the me$^v$-αQ$_1$ antibody appears to binds preferentially to the quadruplex [(TET4)$_4$] (SEQ ID NO:3)$_4$.

Figure 1:
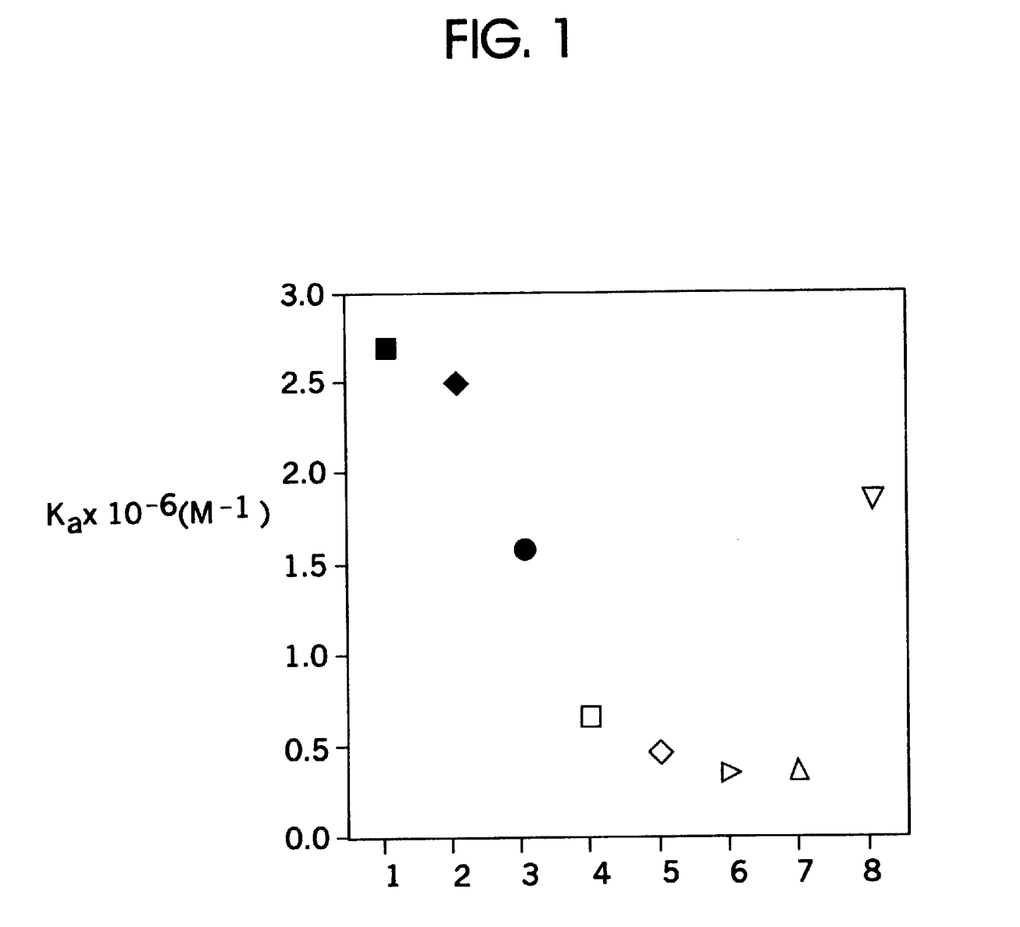
FIG. 1 is a graphical representation of the hierarchies of binding affinities of the antibody $me^v$-$\alpha Q_1$ for several different nucleic acid structures.

Binding affinities of the anti-quadruplex antibody me$^v$-αQ$_1$ for several DNA structures were determined by Scatchard analysis (G. Scatchard, *Ann. N.Y. Acad. Sci.* 51, 660–72 (1949)) of the RIFB results. The value K$_a$ characterizes the macroscopic binding constant and capacity for a nucleic acid substrate, while the value K$_{a, avg}$ characterizes the population-averaged single-site value of the equilibrium association constant.

me$^v$-αQ$_1$ binds quadruplexes with an average affinity that is at least five-fold higher than for other common DNA structures, as shown below in Table 1 and in FIG. 1. FIG. 1 illustrates the affinity hierarchy and range of me$^v$-αQ$_1$ for different types of nucleic acid structures. Based upon the overall association constants determined from the Scatchard plot slopes, the binding hierarchy of quadruplexes for me$^v$-αQ$_1$ is [(TET4)$_4$] (SEQ ID NO:3)$_4$>[d(TG$_4$)$_4$] (SEQ ID NO:2)$_4$>>[d(CGC G$_4$ GCG)$_4$] (SEQ ID NO:1)$_4$. Association constants (K$_a$) for [(TET4)$_4$] (SEQ ID NO:3)$_4$, [d(TG$_4$)$_4$] (SEQ ID NO:2)$_4$, and [d(CGC G$_4$ GCG)$_4$] (SEQ ID NO:1)$_4$ were 2.7×10$^5$, 2.5×10$^6$ and 1.6×10$^6$ M$^{-1}$, respectively. Plotting K$_a$ values for antibody binding as a function of the number of hydrogen-bonded strands in the DNA complexes shows that quadruplexes have the highest affinities of the molecules that were examined (see FIG. 1).

TABLE 1

Scatchard Parameters for Antibody-Substrate Binding[a]

| Substrate | K$_d$ (M) | K$_a$ (M$^{-1}$) | K$_{a\ avg}$ per site (M$^{-1}$) |
|---|---|---|---|
| [(TET4)$_4$] (SEQ ID NO:3)$_4$ | 3.7 × 10$^{-7}$ | 2.7 × 10$^6$ | 1.2 × 10$^5$ |
| [d(TG$_4$)$_4$] (SEQ ID NO:2)$_4$ | 4.0 × 10$^{-7}$ | 2.5 × 10$^6$ | 4.9 × 10$^4$ |
| [d(CGC G$_4$ GCG)$_4$] (SEQ ID NO:1)$_4$ | 6.3 × 10$^{-7}$ | 1.6 × 10$^6$ | 1.5 × 10$^5$ |
| d(G$_4$T$_3$G$_4$T$_3$C$_4$) (SEQ ID NO:11) | 1.5 × 10$^{-6}$ | 6.8 × 10$^5$ | 1.9 × 10$^4$ |
| d(C$_4$T$_3$G$_4$T$_3$G$_4$) (SEQ ID NO:12) | 2.0 × 10$^{-6}$ | 5.0 × 10$^5$ | 1.1 × 10$^4$ |
| [d(CG$_5$)$_2$] (SEQ ID NO:13)$_2$ | 2.6 × 10$^{-6}$ | 3.8 × 10$^5$ | 3.7 × 10$^3$ |
| poly [r(G)] | 2.5 × 10$^{-6}$ | 4.0 × 10$^5$ | 3.1 × 10$^4$ |
| poly [r(C)] | 5.2 × 10$^{-7}$ | 1.9 × 10$^6$ | 1.3 × 10$^4$ |

[a]Results were calculated assuming four-stranded complexes for quadruplex substrates with molecular weights of 30,876, 6,556, and 12,760 Da for [(TET4)$_4$], [d(TG$_4$)$_4$], and [d(CGC G$_4$ GCG)$_4$], respectively. Oligonucleotides d(G$_4$T$_3$G$_4$T$_3$C$_4$) and d(C$_4$T$_3$G$_4$T$_3$G$_4$) were assumed to form intramolecular triplexes of 5,634 Da. Molecular weights of poly [r(G)] (250 kDa) and poly [r(C)] (655 kDa) were mean values for polydispersed mixtures provided by the manufacturer (Sigma). The molecular weight of the me$^v$-aQ$_1$ antibody was assumed to be 1.7 × 10$^6$ Da based on gel filtration and electrophoretic analyses. Note that although poly [r(C)] produced a K$_a$ value of 19 × 10$^6$ M$^{-1}$, this binding affinity is misleading because only 0.02% of the substrate is bound under saturating conditions. The polymer can bind to approximately 150 sites per antibody molecule, indicating that the binding that occurs with poly [r(C)] occurs with little specificity.

The foregoing Examples are illustrative of the present invention, and are not to be construed as limiting thereof. The invention is defined by the following claims, with equivalents of the claims to be included therein.

That which is claimed is:

1. A method of binding quadruplex nucleic acid, comprising:

providing a monoclonal antibody that selectively binds to quadruplex nucleic acid; and then contacting quadruplex nucleic acid to said antibody to form an antibody-quadruplex nucleic acid complex.

2. A method according to claim 1, wherein said antibody selectively binds to quadruplex DNA.

3. A method according to claim 1, wherein said binding step is followed by the step of:

detecting said antibody-quadruplex nucleic acid complex.

4. A method according to claim 3, wherein said detecting step is carried out by a radio-immuno-filter binding assay.

5. A method according to claim 1, further comprising the step of:

collecting said quadruplex nucleic acid from said antibody-quadruplex nucleic acid complex.

6. A method according to claim 5, wherein said antibody is immobilized on a solid support, and wherein said collecting step is carried out by eluting said quadruplex nucleic acid from said solid support.

7. A method according to claim 1, wherein said antibody selectively binds to the [d(TTGGGGTTGGGGTTGGGGTTGGGG)$_4$] ((SEQ ID NO:3)$_4$) quadruplex DNA.

8. A method according to claim 1, wherein said antibody selectively binds to the [d(TGGGG)$_4$] ((SEQ ID NO:2)$_4$) quadruplex DNA.

9. A method according to claim 1, wherein said antibody selectively binds to the [d(CGCGGGGGCG)$_4$] ((SEQ ID NO:1)$_4$) quadruplex DNA.

* * * * *

UNITED STATES PATENT AND TRADEMARK OFFICE
CERTIFICATE OF CORRECTION

PATENT NO.    : 6,001,657
DATED         : December 14, 1999
INVENTOR(S)   : Hardin et al.

It is certified that error appears in the above-identified patent and that said Letters Patent is hereby corrected as shown below:

<u>Title page,</u>
Item [75], Inventors, the following should be included:
-- Leonard D. Schultz, Bar Harbour, Maine --

Signed and Sealed this

Twenty-ninth Day of July, 2003

JAMES E. ROGAN
*Director of the United States Patent and Trademark Office*

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 10 base pairs
        (B) TYPE: nucleic acid
        (C) STRANDEDNESS: single
        (D) TOPOLOGY: Not Relevant     (ii) MOLECULE TYPE: DNA (genomic)

(xi) SEQUENCE DESCRIPTION: SEQ ID NO:1:

CGCGGGGGCG                                                              10

(2) INFORMATION FOR SEQ ID NO:2:

(i) SEQUENCE CHARACTERISTICS:
        (A) LENGTH: 5 base pairs
        (B) TYPE: nucleic acid
        (C) STRANDEDNESS: single
        (D) TOPOLOGY: Not Relevant     (ii) MOLECULE TYPE: DNA (genomic)

(xi) SEQUENCE DESCRIPTION: SEQ ID NO:2:

TGGGG                                                                   5

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: Not Relevant     (ii) MOLECULE TYPE: DNA (genomic)

(xi) SEQUENCE DESCRIPTION: SEQ ID NO:3:

TTGGGGTTGG GGTTGGGGTT GGGG                                              24

(2) INFORMATION FOR SEQ ID NO:4:

(i) SEQUENCE CHARACTERISTICS:
        (A) LENGTH: 6 base pairs
        (B) TYPE: nucleic acid
        (C) STRANDEDNESS: single
        (D) TOPOLOGY: Not Relevant     (ii) MOLECULE TYPE: DNA (genomic)

(xi) SEQUENCE DESCRIPTION: SEQ ID NO:4:

TTAGGG                                                                  6

(2) INFORMATION FOR SEQ ID NO:5:

(i) SEQUENCE CHARACTERISTICS:
        (A) LENGTH: 9 base pairs
        (B) TYPE: nucleic acid
        (C) STRANDEDNESS: single
        (D) TOPOLOGY: Not Relevant     (ii) MOLECULE TYPE: DNA (genomic)

(xi) SEQUENCE DESCRIPTION: SEQ ID NO:5:

CGCGGGGCG                                                               9

(2) INFORMATION FOR SEQ ID NO:6:

(i) SEQUENCE CHARACTERISTICS:
        (A) LENGTH: 10 base pairs
        (B) TYPE: nucleic acid
        (C) STRANDEDNESS: single
        (D) TOPOLOGY: Not Relevant     (ii) MOLECULE TYPE: DNA (genomic)

(xi) SEQUENCE DESCRIPTION: SEQ ID NO:6:

TATGGGGATA                                                              10

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: Not Relevant     (ii) MOLECULE TYPE: DNA (genomic)

(xi) SEQUENCE DESCRIPTION: SEQ ID NO:7:

AGGGGGGGAG AGGGGGGAGG GGGG    24

(2) INFORMATION FOR SEQ ID NO:8:

(i) SEQUENCE CHARACTERISTICS:
        (A) LENGTH: 7 base pairs
        (B) TYPE: nucleic acid
        (C) STRANDEDNESS: single
        (D) TOPOLOGY: Not Relevant     (ii) MOLECULE TYPE: DNA (genomic)

(xi) SEQUENCE DESCRIPTION: SEQ ID NO:8:

TTTAGGG    7

(2) INFORMATION FOR SEQ ID NO:9:

(i) SEQUENCE CHARACTERISTICS:
        (A) LENGTH: 8 base pairs
        (B) TYPE: nucleic acid
        (C) STRANDEDNESS: single
        (D) TOPOLOGY: Not Relevant     (ii) MOLECULE TYPE: DNA (genomic)

(xi) SEQUENCE DESCRIPTION: SEQ ID NO:9:

TTTTGGGG    8

(2) INFORMATION FOR SEQ ID NO:10:

(i) SEQUENCE CHARACTERISTICS:
        (A) LENGTH: 5 base pairs
        (B) TYPE: nucleic acid
        (C) STRANDEDNESS: single
        (D) TOPOLOGY: Not Relevant     (ii) MOLECULE TYPE: RNA (genomic)

(xi) SEQUENCE DESCRIPTION: SEQ ID NO:10:

UGGGG    5

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: Not Relevant     (ii) MOLECULE TYPE: DNA (genomic)

(xi) SEQUENCE DESCRIPTION: SEQ ID NO:11:

GGGGTTTGGG GTTTCCCC    18

(2) INFORMATION FOR SEQ ID NO:12:

(i) SEQUENCE CHARACTERISTICS:
        (A) LENGTH: 18 base pairs

```
            (B) TYPE: nucleic acid
            (C) STRANDEDNESS: single
            (D) TOPOLOGY: Not Relevant (ii) MOLECULE TYPE: DNA (genomic)

(xi) SEQUENCE DESCRIPTION: SEQ ID NO:12:

CCCCTTTGGG GTTTGGGG                                                       18

(2) INFORMATION FOR SEQ ID NO:13:

(i) SEQUENCE CHARACTERISTICS:
            (A) LENGTH: 10 base pairs
            (B) TYPE: nucleic acid
            (C) STRANDEDNESS: single
            (D) TOPOLOGY: Not Relevant (ii) MOLECULE TYPE: DNA (genomic)

(xi) SEQUENCE DESCRIPTION: SEQ ID NO:13:

CGCGCGCGCG                                                                10
```